United States Patent
Rekaya et al.

(10) Patent No.: US 9,999,732 B2
(45) Date of Patent: Jun. 19, 2018

(54) DRUG INJECTION DEVICE WITH PARTICULAR OPTICAL WINDOW ELEMENTS FOR UNAMBIGUOUS LEGIBILITY OF DOSE VALUE

(71) Applicant: Sanofi-Aventis Deutschland GmbH, Frankfurt am Main (DE)

(72) Inventors: Naceur Rekaya, Warwickshire (GB); David Aubrey Plumptre, Worcestershire (GB); Paul Richard Draper, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 326 days.

(21) Appl. No.: 14/773,325

(22) PCT Filed: Mar. 10, 2014

(86) PCT No.: PCT/EP2014/054527
§ 371 (c)(1),
(2) Date: Sep. 5, 2015

(87) PCT Pub. No.: WO2014/139915
PCT Pub. Date: Sep. 18, 2014

(65) Prior Publication Data
US 2016/0058951 A1     Mar. 3, 2016

(30) Foreign Application Priority Data
Mar. 13, 2013   (EP) ..................................... 13159049

(51) Int. Cl.
*A61M 3/00* (2006.01)
*A61M 5/315* (2006.01)
(Continued)

(52) U.S. Cl.
CPC .......... *A61M 5/31525* (2013.01); *A61M 5/24* (2013.01); *A61M 2005/3126* (2013.01); *A61M 2205/58* (2013.01); *A61M 2205/585* (2013.01)

(58) Field of Classification Search
CPC ...... A61M 2005/3126; A61M 2205/58; A61M 2205/585; A61M 5/24; A61M 5/31525
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 A2 | 8/1999 |
| EP | 0937476 A2 | 8/1999 |

(Continued)

OTHER PUBLICATIONS

Office Action issued in Chinese Patent Application No. 201480013616.0 dated Jun. 28, 2017.
(Continued)

*Primary Examiner* — Jason Flick
(74) *Attorney, Agent, or Firm* — Fish & Richardson P.C.

(57) ABSTRACT

An arrangement comprising an optical element and an indication member for a drug delivery device is provided. The indication member comprises a plurality of indicia. The optical element comprises an imaging section and a light-transmissive non-imaging section, wherein the indication member is movable with respect to the optical element such that the indicia can be successively moved into a display position relative to the optical element. The imaging section is configured such that, when a first indicium is arranged in the display position, the first indicium is imaged by the imaging section into an imaging solid angle. The non-
(Continued)

imaging section is configured such that light defining a second indicium is deflected by the non-imaging section such that the second indicium cannot be identified by a user in the imaging solid angle on a viewing side of the optical element.

15 Claims, 3 Drawing Sheets

(51) Int. Cl.
*A61M 5/24* (2006.01)
*A61M 5/31* (2006.01)

(58) Field of Classification Search
USPC .......................................................... 604/189
See application file for complete search history.

(56) References Cited

U.S. PATENT DOCUMENTS

| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,001,082 | A | 12/1999 | Dair et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2005/0177114 | A1 | 8/2005 | Michel et al. |
| 2006/0153693 | A1 | 7/2006 | Fiechter et al. |
| 2008/0103435 | A1 | 5/2008 | Graf et al. |
| 2009/0275916 | A1 | 11/2009 | Harms et al. |
| 2010/0274198 | A1 | 10/2010 | Bechtold |
| 2011/0276006 | A1* | 11/2011 | Matthias ............ A61M 5/31525 604/189 |
| 2012/0046613 | A1* | 2/2012 | Plumptre ............ A61M 5/31511 604/189 |

FOREIGN PATENT DOCUMENTS

| EP | 2201973 | A1 | 6/2010 |
| WO | 9311813 | A1 | 6/1993 |
| WO | 9938554 | A1 | 8/1999 |
| WO | 0110484 | A1 | 2/2001 |
| WO | 2008058665 | A1 | 5/2008 |

OTHER PUBLICATIONS

Communication Pursuant to Article 94(3) EPC issued in European Patent Application No. 14710228.9 dated Oct. 20, 2017.

* cited by examiner

DRUG INJECTION DEVICE WITH PARTICULAR OPTICAL WINDOW ELEMENTS FOR UNAMBIGUOUS LEGIBILITY OF DOSE VALUE

CROSS REFERENCE TO RELATED APPLICATIONS

The present application is a U.S. National Phase application pursuant to 35 U.S.C. § 371 of International Application No. PCT/EP2014/054527 filed Mar. 10, 2014, which claims priority to European Patent Application No. 13159049.9 filed Mar. 13, 2013. The entire disclosure contents of these applications are herewith incorporated by reference into the present application.

FIELD OF INVENTION

Arrangement for a Drug Delivery Device

The present disclosure relates to an arrangement for a drug delivery device, e.g. an injector-type device, such as a pen-type injector. Furthermore, the present disclosure relates to a drug delivery device.

BACKGROUND

For example, a drug delivery device is known from WO 2008/058665 A1.

It is an object of the present disclosure to facilitate identification of indicia of a drug delivery device.

This object is achieved by the subject-matter of the independent claim. Advantageous embodiments and refinements are subject-matter of the dependent claims.

SUMMARY

One aspect of the present disclosure relates to an arrangement for a drug delivery device, such as an injector-type device. The arrangement comprises an optical element and an indication member for a drug delivery device. The indication member comprises a plurality of indicia. The optical element comprises an imaging section and a non-imaging section. The indication member is movable with respect to the optical element such that the indicia can be successively moved into a display position relative to the optical element.

In an embodiment, the imaging section is configured such that, when the first indicium is arranged in the display position, the first indicium is imaged by the imaging section into an imaging solid angle.

The viewing side of the optical element may be a side of the optical element which faces away from the indication member. Thereby, the indication member may be arranged on a side of the optical element which is opposite to the viewing side.

In an embodiment, the non-imaging section is configured such that light defining the second indicium, e.g. light reflected from the indication member, is deflected by the non-imaging section such that the second indicium cannot be identified by a user in the imaging solid angle on the viewing side of the optical element. Expediently, the imaging section is transparent.

In an embodiment, the non-imaging section is light-transmissive.

A further aspect of the present disclosure relates to a drug delivery device comprising the arrangement, wherein the optical element is designed to form a dose window of the drug delivery device. The dose window may, e.g., be provisioned to allow the user to view or inspect dose indicia of the drug delivery device which may be provided on an inner part of the drug delivery device such as the indication member. The distance between the indication member and the optical element may span a range between about 0.2 millimeter, e.g. in a central region of the optical element, and 0.3 millimeter, e.g. in a peripheral region of the optical element. The indication member may be a display member of the drug delivery device. The drug delivery device may comprise a needle or a needle assembly through or via which a drug may be dispensed from the drug delivery device.

In an embodiment, the arrangement is configured such that during a dose set and/or a dose dispense operation of the drug delivery device, different indicia can be moved into the display position. Thereby, the indication member may be moved with respect to the optical element or vice versa.

Light, particularly visible light, defining indicia may mean that, said light defines a contour of the indicia. Thereby, the indicia itself and the region surrounding the indicia may reflect the light differently such that said contour becomes visible. Consequently, the light may either be reflected from the indicia or from the region surrounding the indicia.

Preferably, the display position of an indicium is a position in which a dose or a size of a dose of the drug delivery device corresponding to this indicium is set and wherein the user can positively identify said indicium through the optical element in the imaging solid angle.

The imaging solid angle is a solid angle in which the indicium, which is arranged in the display position, can be positively identified by the user. An image which is generated by the imaging section may thereby be defined or confined by the imaging solid angle, wherein the imaging solid angle extends over the image. Said image may relate to the first indicium when the first indicium is arranged in the display position.

From a manufacturing point of view, it may be expedient to form a housing of the drug delivery device and the dose window from a single component. This means that the housing would be transparent and requires an opaque covering. To this effect, a printing or over-labeling of the housing would usually leave a gap around the dose window. When a certain dose is set by the drug delivery device and an indicium corresponding to this dose is indicated through the dose window, it is possible that markings, characters or another indicium which is not arranged in the display position is visible through the gap. This may cause confusion to the user when a dose is set. If the dose window is configured as a magnifying lens, said markings or indicia may appear misaligned and in this way cause considerable confusion to the user.

With the present disclosure, it is achieved that, when the first indicium is arranged in the display position, the first indicium is visible for the user while the second indicium which may be arranged adjacent to the first indicium cannot be identified by the user. In this way, confusion of the user is prevented, as the second indicium—which may be arranged adjacent to the first indicium or any other markings—cannot be identified by the user in the imaging solid angle on a viewing side of the optical element.

In an embodiment, the indicia comprise numbers, such as dose numbers and/or non-numerical characters, wherein the non-numerical characters preferably separate adjacent numbers. The non-numerical characters may comprise symbols, such as dashes.

Preferably, the first indicium comprises a dose number and the second indicium which may be adjacent to the first indicium comprises a dash, separating the first indicium from a further indicium. Alternatively, the first and the second indicium may both exhibit dose numbers, indicating subsequent sizes of set doses or quantities of drug to be dispensed from the drug delivery device. Subsequent sizes may differ from each other by, e.g. two units, four units, or just one unit. A unit may relate to a minimum amount of drug which may be set to be dispensed by the drug delivery device. The indicia may, e.g. be printed, on the outer surface of the indication member.

In an embodiment, the non-imaging section surrounds the imaging section, particularly, as seen in plane view from the viewing side. The non-imaging section may define a boundary area of the optical element. As an advantage, it is easily achieved independent from the mutual arrangement of the first indicium and the second indicium that the first indicium is imaged by the imaging section while the second indicium cannot be identified by the user in the imaging solid angle on a viewing side of the optical element, provided that the first indicium is arranged in the display position.

In an embodiment, the optical element is comprised by a body and the arrangement comprises a covering which defines a window, wherein the window is arranged and configured such that the optical element is visible through the window. Preferably, the covering covers the body in a region different from the region where the optical element is situated. Apart from the optical element, the body may be opaque or translucent or partly opaque or translucent. Alternatively, the body may be transparent. Preferably, the body is transparent.

In a preferred embodiment, the covering is opaque. This is particularly expedient, if the body is embodied transparent such that the covering can define the window. Thereby, it is achieved that a user can see through the window or, as the case may be the optical element while structures which are not covered by the window are not visible to the user or blanked. As an advantage, the attention of the user may be focussed to structures or elements, as. e.g. indicia which are made visible through the window and/or the optical element, e.g. from the outside of the drug delivery device.

In the present disclosure, "transparent" may relate to the property of structures through which objects—including its contours—may be viewed or resolved by a user or an observer. "Translucent" may relate to the property of structures which are partly light-transmissive, such that contours of objects may not be viewed or resolved.

The body may constitute an outer housing of the drug delivery device. Preferably, the user cannot identify any features of the drug delivery device which are not covered by the window.

In an embodiment, the imaging section extends over the first indicium when the first indicium is arranged in the display position.

In an embodiment, the non-imaging section at least partly extends over the second indicium when the first indicium is arranged in the display position. In other words, the projection of the imaging section on the indication member extends over the first indicium when the first indicium is arranged in the display position and the projection of the non-imaging section at least partly extends over the second indicium when the first indicium is arranged in the display position. Thus, the projection of the optical element on the indication member may extend over the first indicium and partly also over the second indicium or any further indicium which may be arranged adjacent to the first indicium.

In an embodiment, the imaging section is elevated as compared to the non-imaging section. This embodiment may advantageously enable the embodiment of the imaging section according to specific imaging requirements of the imaging section. For example, the elevation of the imaging section facilitates an embodiment of the imaging section as or in accordance with a magnifying element. Additionally, a side wall of the imaging section which may be present due to the elevation may reflect light which defines the second indicium. Thereby, the elevation may facilitate that said light is deflected such that the light cannot be identified by the user in the imaging solid angle.

In an embodiment, the imaging section is formed in accordance with a magnifying element, such as a lens. As an advantage of this embodiment, readability of indicia may be improved, especially for persons with poor eyesight, as for instance elderly persons. Also, said embodiment may be advantageous for diabetics which often suffer from poor eyesight.

When the imaging section is embodied as a magnifying element, the user may view the first indicium magnified in the viewing solid angle when the first indicium is arranged in the display position.

In an embodiment, the non-imaging section is a transparent refractive section which comprises a boundary surface. The boundary surface is arranged and configured such that, when the first indicium is arranged in the display position, the second indicium cannot be identified by the user in the imaging solid angle on the viewing side of the optical element.

In an embodiment, the boundary surface comprises a plane or an even portion which is obliquely oriented with respect to an optical axis of the arrangement.

In the present disclosure, "oblique" or "obliquely" preferably means that a component is not arranged or oriented perpendicularly with respect to another component.

The optical axis may be an axis along which the optical element and the first indicium are aligned when the first indicium is arranged in the display position.

Due to the oblique orientation of the boundary surface of the non-imaging section, light emitted or reflected from the indication member and passing through the optical element may be refracted differently from the non-imaging section, as compared to the imaging section, such that light defining the second indicium and which passes through the non-imaging section is deflected in an area outside of the viewing solid angle.

In an embodiment, the boundary surface comprises a structured surface which is configured such that, when the first indicium is arranged in the display position, there is a first solid angle outside of the imaging solid angle on a viewing side of the optical element into which the second indicium is imaged by the structured surface, wherein the second indicium cannot be identified by the user in a second solid angle on the viewing side which is arranged outside of the imaging solid angle and which is different from the first solid angle.

Preferably, the non-imaging section is configured such that the boundary surface surrounds the imaging section. The structured surface may comprise a plurality of planes or even portions, the surface normals of which are inclined with respect to each other and/or with respect to the optical axis. On the viewing side of the optical element, one or more surface normals of the portions are preferably directed away from the optical axis such that light emitted or reflected from the indication member and defining a second indicium while the first indicium is in the display position, is deflected by the boundary surface such that the second indicium cannot be identified by the user in the imaging solid angle on the viewing side of the optical element. In other words, the boundary surface may deflect light defining the second indicium out of the viewing solid angle. Thus, only the first indicium can be identified by the user in the imaging solid angle.

The even portions may be suitable to image, e.g. the second indicium, when the first indicium, being arranged adjacent to the second indicium, is in the display position. Advantageously, the user is not confused by the second indicium or further indicia or markings when reading or inspecting the set dose or the size of the set dose of the drug delivery device in a solid angle outside of the viewing solid angle.

In an embodiment, the non-imaging section is a translucent diffusive section. According to this embodiment, it can advantageously be achieved that, when the first indicium is arranged in the display position, the first indicium is imaged by the imaging section into the imaging solid angle and that the second indicium cannot be identified by the user, as it is not imaged but diffused by the non-imaging section. The translucent diffusive section may comprise a roughened surface which prevents an imaging of the second indicium when the first indicium is arranged in the display position. Said roughened surface may comprise a surface texture with features having dimensions on the micrometer scale, e.g. one or more micrometers up to 1 millimeter, such that light emitted or reflected from the indication member and passing through the non-imaging section, is diffused.

In an embodiment, the non-imaging section is provided along opposite sides of the optical element. Said opposite sides may face a proximal and/or a distal end of the arrangement. This is particularly expedient, when, e.g. a dash separating two dose numbers is also arranged accordingly on the indication member, i.e. at sides of the first indicium which face the proximal and/or to the distal end of the arrangement, when the first indicium is arranged in the display position. On the remaining sides of the optical element, a non-imaging section may not be required, as at the corresponding sides of the first indicium on the indication member, there may be no indicium provided which could be imaged in the imaging solid angle.

A longitudinal axis of the arrangement may extend from the distal to the proximal end of the arrangement. The longitudinal axis of the arrangement may coincide with the longitudinal axis of the drug delivery device. The distal end of the arrangement may be or face towards a distal end of the drug delivery device and the proximal end of the arrangement may be or face towards a proximal end of the drug delivery device.

The distal end of the drug delivery device may refer to an end at which drug may be dispensed from the drug delivery device and/or at which the needle may be arranged.

The proximal end of the drug delivery device may refer to an end at which is arranged furthest away from where drug may be dispensed from the drug delivery device and/or furthest away from the needle.

BRIEF DESCRIPTION OF THE DRAWINGS

Features which are described herein above and below in conjunction with different aspects or embodiments, may also apply for other aspects and embodiments. Further features and advantageous of the subject matter of the disclosure will become apparent from the following description of the exemplary embodiment in conjunction with the figures, in which.

DETAILED DESCRIPTION

Figure 1:
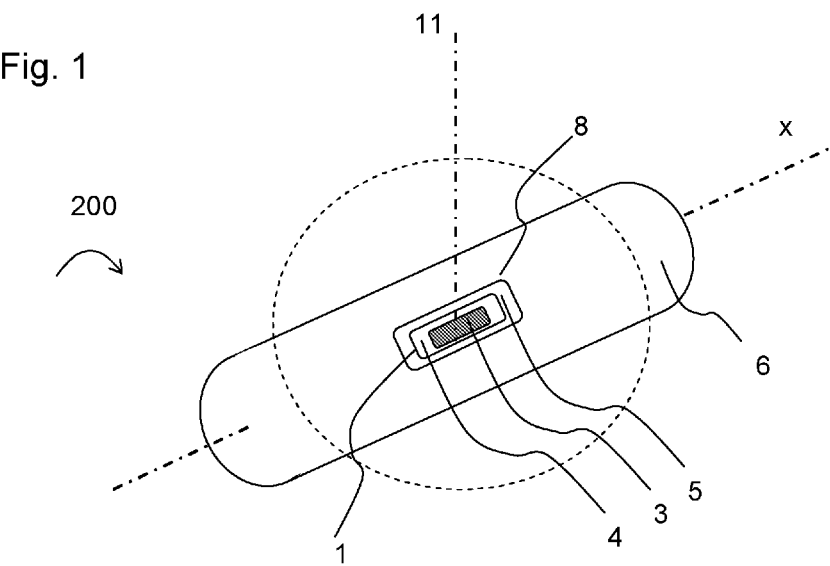
FIG. 1 shows a schematic view of a drug delivery device.

Like elements, elements of the same kind and identically acting elements may be provided with the same reference numerals in the figures. Additionally, the figures may be not true to scale. Rather, certain features may be depicted in an exaggerated fashion for better illustration of important principles.

FIG. 1 shows a schematic illustration of a drug delivery device 200. The drug delivery device 200 may be an injector-type device, such as a pen-type injector. The device may be operable such that fixed or variable doses, preferably doses of a user settable size, of drug may be set and dispensed by a user. The drug delivery device 200 comprises a body 6 and a covering 19 (cf. FIG. 2) defining a window 8. The covering 19 may be opaque. Through the window 8 the actually set dose is preferably visible for the user. The body 6 further comprises an optical element 1 having a rectangular-like shape as seen in plan view. The optical element 1 is designed to form a dose window of the drug delivery device 200 in which dose information, as e.g. the size of a set dose, is displayed to the user. The optical element 1 is visible within the window 8. The covering 19 may cover the body 6 in a region different from the region where the optical element 1 is situated. The optical element 1 comprises an imaging section 4 and a non-imaging section 5. The imaging section 4 is preferably transparent to visible light. The non-imaging section 5 is preferably transmissive to visible light. The non-imaging section 5 surrounds the imaging section 4. The optical element 1 is framed by the window 8. Preferably, the arrangement is thereby fixed to the body 6. The drug delivery device 200 further comprises an indication member 2 which is provided with a plurality of indicia, particularly dose numbers 3. The indication member 2 which is arranged inside the body 6 may form a display member of the drug delivery device. In the described situation, a dose number 3 is arranged in a display position relative to the optical element 1. In this situation, the dose number 3 is imaged by the imaging section 4 into an imaging solid angle 9. The imaging solid angle 9 exhibits a solid angle in which the indicium 3 can be easily and positively inspected or viewed by the user of the drug delivery device 200 from a viewing side of the optical element 1. The viewing side (cf. 13 in FIG. 2) of the optical element 1 is a side of the optical element 1 which faces away from the indication member 2. The viewing side 13 is on the outside of the drug delivery device 200.

The indicium 3 may indicate the size of a set dose of the drug delivery device 200, e.g. the number of units of drug which are set to be dispensed. The indication member 2 comprising the dose numbers 3 may be movable with respect to the optical element 1 during a dose setting and/or a dose dispensing operation of the drug delivery device 200 such that an dose number adjacent to the depicted dose number 3 is moved into the display position. The mentioned movement may be an axial or a helical movement of the optical element 1 or a rotation around a longitudinal axis x of the drug delivery device 200. Accordingly, the dose numbers may be arranged or aligned axially, helically or angularly around an outer circumference of the indication member 2 (cf. FIG. 3). The longitudinal axis of the drug delivery device 200 may extend between a distal end and a proximal end of the drug delivery device 200.

Figure 2:
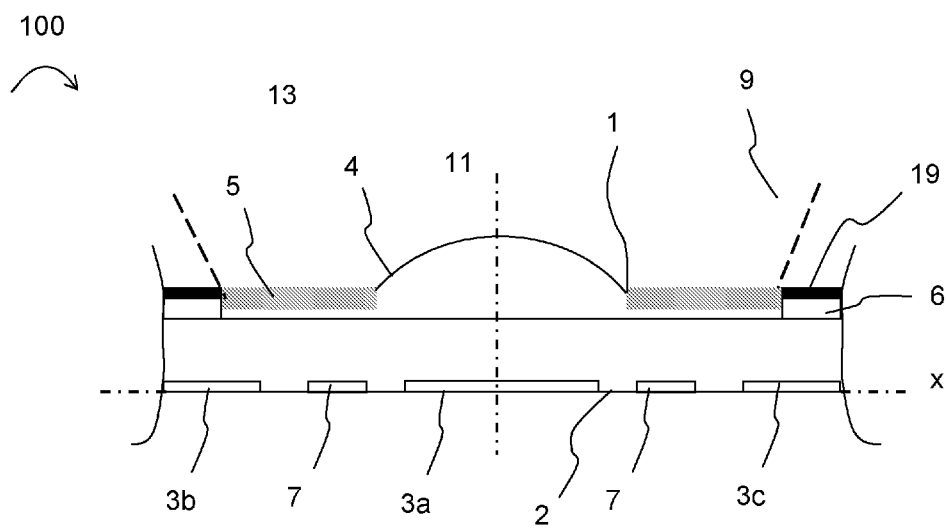
FIG. 2 shows a partial schematic section of an arrangement.

FIG. 2 shows the arrangement 100 comprising the optical element 1 in a schematic section. The drug delivery device 200 may comprise the arrangement 100. The optical element 1 comprises the imaging section 4 and the non-imaging section 5. Due to the sectional illustration in FIG. 2, the imaging section 4 appears to be arranged between two portions of the non-imaging section 5. The longitudinal axis x of the drug delivery device 200 may coincide with a longitudinal axis of the arrangement 100. The indication member 2 is provided with a plurality of indicia which are represented in this embodiment, but not limited thereto by a first dose number 3a and with a second dose number 3b and 3c. Further indicia are represented here by dashes 7 which are arranged adjacent to the dose numbers 3a, 3b and 3c. The direction along which the dose numbers 3a, 3b and 3c are aligned (horizontal direction) may be parallel to the longitudinal axis x. The dose number 3a which may represent a first indicium faces the imaging section 4 of the optical element 1. In the situation depicted in FIG. 2, the first indicium 3a is arranged in the display position relative to the optical element 1 and can thus be identified by the user in the imaging solid angle 9. An optical axis 11 is indicated in FIG. 2 which may run through a center of the imaging section 4. The optical axis 11 may further run radially with respect to the longitudinal axis x. The imaging section 4 or a projection of the imaging section 4 on the indication member 2 extends along the dose number 3a. The optical element 1 extends along the dose number 3a, the dashes 7 and partly along the dose numbers 3b and 3c. The distance between the indication member 2 and the optical element 1 may span a range between about 0.2 millimeter and 0.3 millimeter.

The oblique dashed lines on each side of the arrangement 100 in FIG. 2 indicate the imaging solid angle 9. The imaging section 4 of the optical element 1 is elevated as compared to the non-imaging section 5. As an advantage of this elevation, the imaging section 4 may be configured, e.g. according to a magnifying lens, as indicated by the curved surface of the imaging section 4. Accordingly, the dose number 3a may be magnified to the user, when the user reads or identifies the dose number 3a.

The imaging section 4 is configured such that the dose number 3a is imaged by the imaging section 4 into the imaging solid angle 9. The non-imaging section 5 is configured such that light defining the dose numbers 3b and 3c and/or the dashes 7, i.e. elements on the indication member which are not in the display position, is deflected by the non-imaging section 5 such that said elements cannot be identified by the user in the imaging solid angle 9 on the viewing side 13 of the optical element 1. The arrangement 100 may be configured such that when the size of a dose of drug which may be indicated by the dose number 3a—and which is imaged by the imaging section 4—is varied by the user, the indication member 2 may be moved such that the dose number 3a is moved out of the display position. Consequently, one of the dose numbers 3b and 3c is moved into the display position. Thus, this indicium will then be imaged by the imaging section into the imaging solid angle 9.

Figure 3:
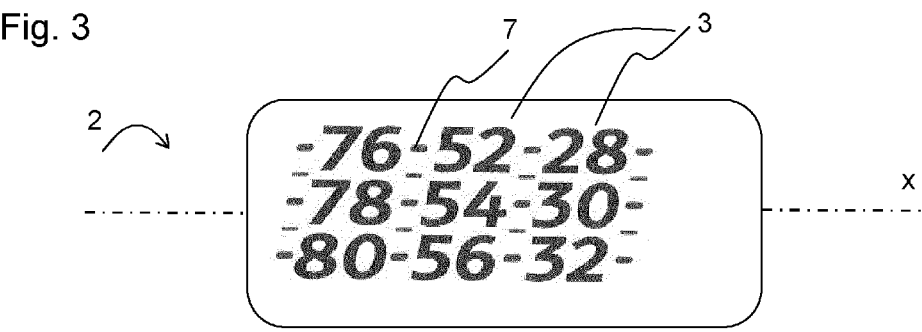
FIG. 3 shows an exemplary embodiment of dose indicia.

FIG. 3 shows a partial simplified top view of the indication member 2 comprising exemplary dose numbers 3 and dashes 7. The dose number 3 and the dashes 7 which separate the indicia 3 are aligned along an axis parallel to the longitudinal axis x, respectively. The indicia 3 are arranged helically, whereby two vertically or circumferentially consecutive indicia indicate a difference of two dose units. In FIG. 3, only a fraction of possible indicia is indicated schematically.

Figure 4:
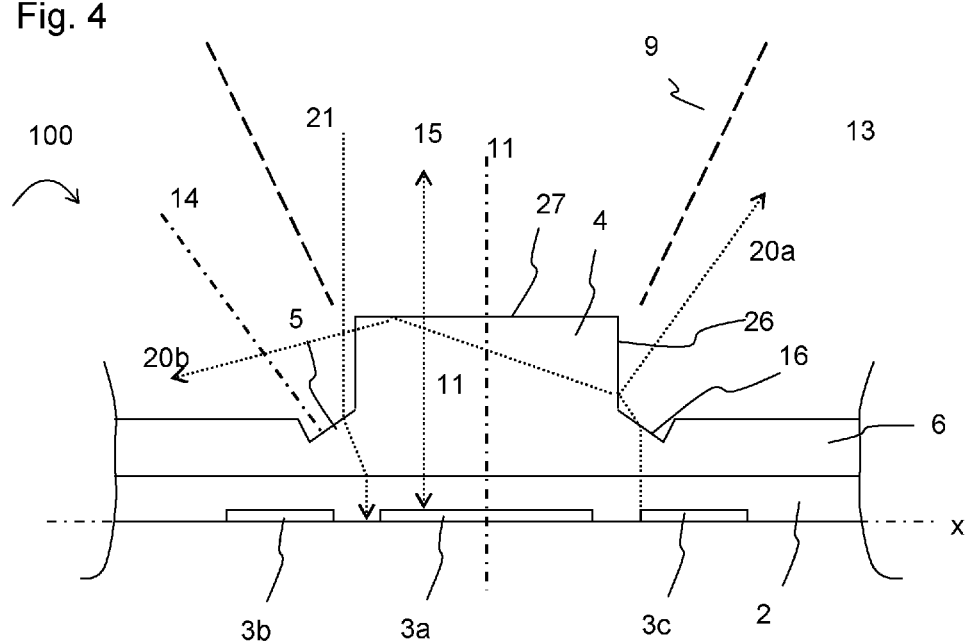
FIG. 4 shows a partial schematic section of the arrangement by means of an exemplary embodiment.

FIG. 4 shows a partial schematic section of the arrangement 100, wherein the dose number 3a is in the display position comparable to the situation shown in FIG. 2. The imaging section 4 is again elevated as compared to the non-imaging section 5. The imaging section 4 is preferably formed according to a magnifying lens. A side wall 26 of the imaging section runs between the imaging section 4 and the non-imaging section 5. The side wall 26 connects the imaging section 4 and the non-imaging section 5. The side wall 26 may define by how much the imaging section 4 is elevated over the non-imaging section 5. The dose number 3a is imaged by the imaging section 4 into the imaging solid angle 9, as is indicated by the optical path 19 such that the user can identify the dose number 3a in the imaging solid angle 9 on a viewing side 13 of the optical element 1. In this embodiment, the non-imaging section 5 is preferably transparent to visible light and comprises a boundary surface 10. The boundary surface 10 may be oriented obliquely with respect to the optical axis 11. The boundary surface 10 may be partially even or comprise a plane or portions 16, e.g. at each of the optical element 1, when the optical element 1 is rectangular. The portions 16 may be even and define surface normals 14 which are inclined with respect to the optical axis 11. Due to the inclination of the boundary surface 10, light defining the dose numbers 3b and 3c is deflected out of the imaging solid angle 9 such that the user cannot identify said dose numbers in the imaging solid angle 9. Although not explicitly indicated, the portions may also be uneven in section. Exemplary optical paths 20a and 20b of light defining the dose number 3c and extending from the indication member 2, are shown in FIG. 4. Light according to the optical path 20a passes through the non-imaging section 5. The light is deflected by the non-imaging section 5 towards an area outside of the viewing solid angle 9 such that the dose numbers 3c cannot be identified in the viewing solid angle 9. The light is thereby refracted and subsequently reflected, at the side wall 26 in a longitudinal direction such that it is deflected away from the optical axis 11. Additionally or alternatively, light running according to the optical path 20b may re-enter into the imaging section of the optical element 1 after having passed the non-imaging section 5. Then, the light may also be reflected, as e.g. totally reflected at a surface 27 of the imaging section 4 such that it does not leave the optical element 1 within the imaging solid angle 9.

On the other hand, light according to an optical path 21 originating from the viewing side 13 is refracted by the non-imaging section 5 and passes through the same. When the light subsequently exits the non-imaging section 5, it may be deflected again such that it does not meet the dose numbers 3b and 3c. In other words, the light is deflected by the non-imaging section 5 due to the inclination of the boundary surface 10 such that only the dose number 3a can be viewed by the user, although the optical element 1 extends in parts also over the dose numbers 3b and 3c. The index of refraction of the non-imaging section 5 may be adjusted accordingly. Due to the inclination of the boundary surface 10 of the non-imaging section 5 of the optical element 1, the dose numbers 3b and 3c cannot be identified by the user in the imaging solid angle 9 on the viewing side 13 of the optical element 1. Outside of the imaging solid angle 9 on the viewing side 13 of the optical element 1, at least fractions of the dose numbers 3b and 3c may be identified by the user, as light defining the second indicia may be deflected accordingly by the boundary surface 10. Although not explicitly indicated, the optical element may also be configured such that the non-imaging section extends only partly along a circumference of the optical element. For example, the non-imaging section may extend, only along sides of the optical element which face a proximal and/or a distal end of the arrangement (cf. in FIG. 5). On the remaining sides of the optical element, a non-imaging section may not be required, as at the corresponding sides of the first indicium on the indication member, there may be no second indicia, provided which could be imaged in the imaging solid angle. In FIG. 4, the dashes 7 separating the dose numbers are omitted. However, the dose numbers 3b and 3c may also be embodied as dashes. Nevertheless, it is advantageous that the non-imaging section 5 extends about the whole circumference of the imaging section 4.

Figure 5:
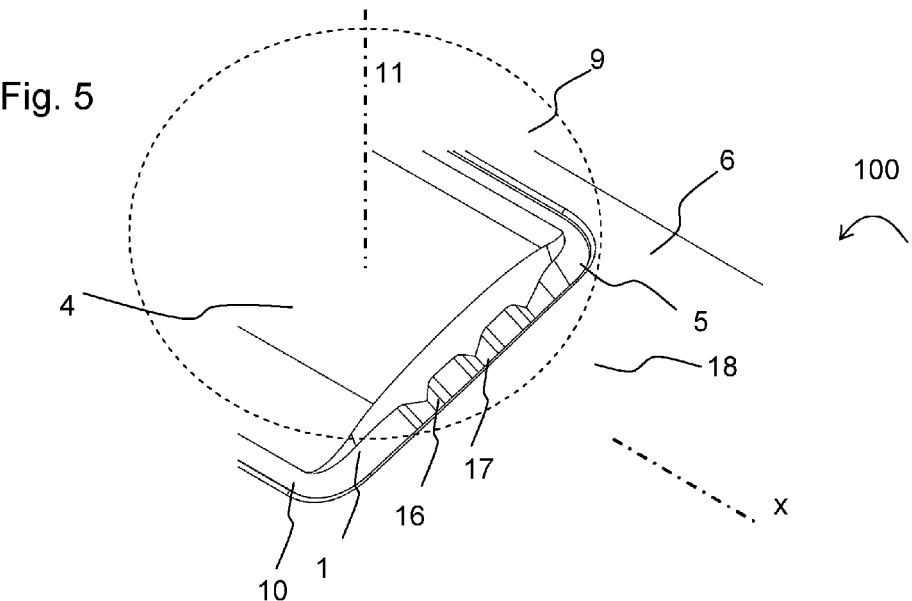
FIG. 5 shows a partial perspective view of the arrangement by means of a further exemplary embodiment.

FIG. 5 shows a partial perspective view of the arrangement 100 by means of a further exemplary embodiment. As described in connection with FIG. 4, the optical element 1 comprising the imaging section 4 and the non-imaging section 5 is preferably transparent to visible light. It is shown in FIG. 5 that the non-imaging section 5 only extends along a side 18 of the optical element 1 which faces a proximal and/or a distal end of the arrangement 100. Accordingly, indicia (not indicated) may in this embodiment also be arranged along the longitudinal axis x. Although not explicitly indicated, the optical element 1 may also be configured such that the non-imaging section 5 surrounds the imaging section 4. The non-imaging section 5 may comprise a boundary surface 10 with a plurality of portions 16. Each portion 16 may be even or a plane. The portions 16 may form a structured surface 17 of the boundary surface 10. In this case, surface normals of the portions 16 may be inclined with respect to the optical axis 11 and/or with respect to one another. Although not explicitly indicated, the portions 16 may also be uneven or curved. Preferably, the portions 16 are configured such that light emitted or reflected from the indication member 2 and passing through the non-imaging section 5, is deflected into a direction which is transverse to the longitudinal axis x. Preferably, the portions 17 image, e.g. the second indicium into a first solid angle (cf. 24 in FIG. 6) outside of the viewing solid angle 9, when the first indicium is in the display position. As an advantage of this embodiment, there may be second solid angles (cf. 25 in FIG. 6) outside of the imaging solid angle 9 from which the second indicia cannot be identified by the user such that the user is not confused, e.g. during the inspection of the size of the set dose.

Figure 6:
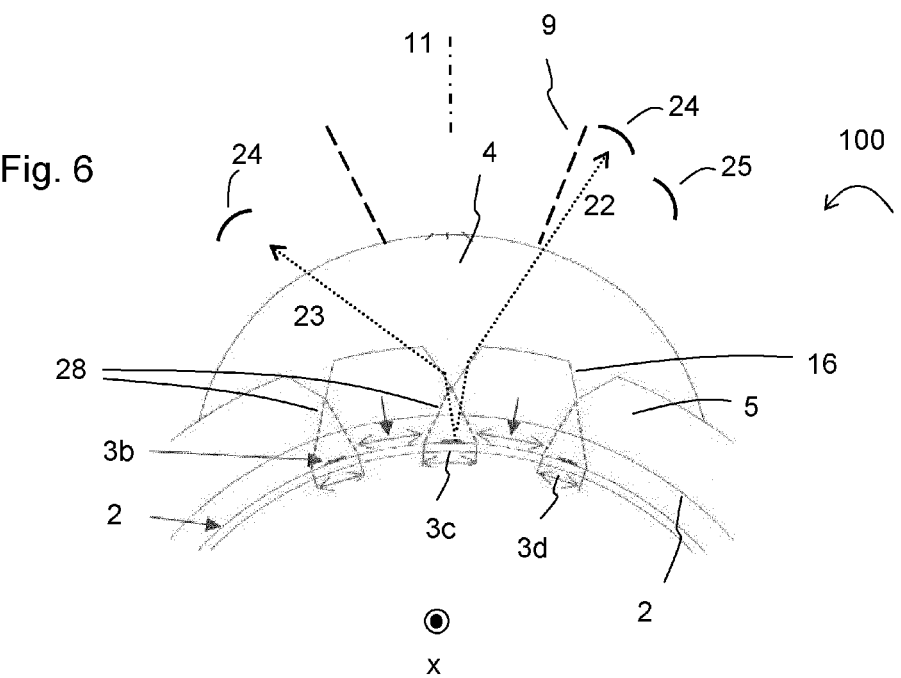
FIG. 6 shows a schematic transverse section of the arrangement according to the embodiment shown in FIG. 5.

FIG. 6 shows a schematic transverse section of the arrangement 100 of the embodiment shown in FIG. 5, wherein the dose number 3a is arranged in the display position. The arrangement 100 is shown curved. This curvature may be determined by the curvature of the drug delivery device 200. In FIG. 6, a cross-section of the non-imaging section 5 from FIG. 5 is shown. The non-imaging section 5 comprises three equilateral cuts defining portions 16 (cf. portions 16 in FIG. 5). When light emitted or reflected from the indication member 2 passes through the non-imaging section 5, it is formed by the portions 16 such that a user cannot identify dose numbers 3b, 3c and 3d may represent a second indicium, respectively. Said dose numbers are preferably arranged adjacent to the dose number 3a (not shown) representing a first indicium. In contrast to the embodiments shown in the FIGS. 2 and 4, the dose numbers 3b, 3c and 3d are not aligned longitudinally but along an outer circumference of the indication member 2. Exemplary optical paths 22 and 23 are shown which indicate that the light emitted or reflected from the indication member 2 is deflected by the portions 16 out of the viewing solid angle 9. Thereby, light according to the optical path 22 undergoes a reflection, as e.g. a total reflection and then exits from the non-imaging section 5, while light according to the optical path 23 is simply refracted by the non-imaging section 5.

Regions on the indication member 2 in which the dose numbers 3b, 3c and 3d are arranged may not be met by light passing through the non-imaging section 5 from the viewing side 13, as the light is deflected away from said regions due to the portions 16 of the non-imaging section 5. The regions are schematically defined by means of the dashed lines 28 next to the indicia 3b, 3c and 3d. The index of refraction of the non-imaging section 5 may be adjusted accordingly. Due to the configuration of the structured surface 17, the dose numbers 3b, 3c and 3d cannot be identified by the user in the imaging solid angle 9 on the viewing side 13 of the optical element 1.

In a further exemplary embodiment, the non-imaging section (cf. FIG. 2) is a translucent diffusive section. To this effect, the non-imaging section may comprise a roughened surface which prevents an imaging of an indicium being arranged adjacent to the first indicium, when the first indicium is arranged in the display position. Said roughened surface may comprises a surface texture with features having dimensions on the micrometer scale, e.g. one or more micrometers up to 1 millimeter, such that light emitted or reflected from the indication member and passing through the non-imaging section, is diffused.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

The invention claimed is:

1. Arrangement comprising an optical element and an indication member for a drug delivery device, the indication member comprising a plurality of indicia, and the optical element comprising an imaging section and a light-transmissive non-imaging section, wherein the indication member is movable with respect to the optical element such that the indicia can be successively moved into a display position relative to the optical element, wherein the imaging section is configured such that, when a first indicium is arranged in the display position, the first indicium is imaged by the imaging section into an imaging solid angle and, wherein the non-imaging section is configured such that light defining a second indicium is deflected by the non-imaging section such that the second indicium cannot be identified by a user in the imaging solid angle on a viewing side of the optical element.

2. Arrangement according to claim 1, wherein the second indicium is arranged adjacent to the first indicium.

3. Arrangement according to claim 1, wherein the non-imaging section surrounds the imaging section.

4. Arrangement according to claim 1, wherein the non-imaging section at least partly extends over the second indicium when the first indicium is arranged in the display position.

5. Arrangement according to claim 1, wherein the optical element is comprised by a body and wherein the arrangement comprises a covering which defines a window, wherein the window is arranged and configured such that the optical element is visible through the window.

6. Arrangement according to claim 5, wherein the covering is opaque.

7. Arrangement according to claim 1, wherein the indicia comprise numbers and non-numerical characters, and wherein the non-numerical characters separate adjacent numbers.

8. Arrangement according to claim 1, wherein the imaging section is elevated, as compared to the non-imaging section.

9. Arrangement according to claim 1, wherein the imaging section is formed in accordance with a magnifying lens.

10. Arrangement according to claim 1, wherein the non-imaging section is a transparent refractive section which comprises a boundary surface which is arranged and configured such that, when the first indicium is arranged in the display position, the second indicium cannot be identified by the user in the imaging solid angle on a viewing side of the optical element.

11. Arrangement according to claim 10, wherein the boundary surface comprises a plane or an even portion which is obliquely oriented with respect to an optical axis of the arrangement.

12. Arrangement according to claim 10, wherein the boundary surface comprises a structured surface which is configured such that, when the first indicium is arranged in the display position, there is a first solid angle outside of the imaging solid angle on the viewing side of the optical element into which the second indicium is imaged by the structured surface, wherein the second indicium cannot be identified by the user in a second solid angle on the viewing side which is arranged outside of the imaging solid angle and which is different from the first solid angle.

13. Arrangement according to claim 1, wherein the non-imaging section is a translucent diffusive section.

14. Arrangement according to claim 4, wherein the non-imaging section is provided along opposite sides of the optical element.

15. Drug delivery device comprising the arrangement according to claim 1, wherein the optical element is designed to form a dose window of the drug delivery device, and wherein the arrangement is configured such that during a dose set operation of the drug delivery device, a dose dispense operation of the drug delivery device, or both the dose set operation and the dose dispense operation, different indicia can be moved into the display position.

* * * * *